United States Patent [19]
Woolnough et al.

[11] Patent Number: 5,997,583
[45] Date of Patent: Dec. 7, 1999

[54] LOWER LIMB PROSTHESIS AND A SHIN COMPONENT FOR THE PROSTHESIS

[75] Inventors: Victor James Woolnough, Hampshire; Andrew John Sear Evans, Surrey, both of United Kingdom

[73] Assignee: Chas. A. Blatchford & Sons Limited, United Kingdom

[21] Appl. No.: 08/947,964

[22] Filed: Oct. 9, 1997

[30] Foreign Application Priority Data

Oct. 10, 1996 [GB] United Kingdom .................. 9621138

[51] Int. Cl.$^6$ .................................................... A61F 2/62
[52] U.S. Cl. ................................ 623/38; 623/27; 623/55
[58] Field of Search .............................. 623/27, 28, 38, 623/35, 47–50, 52, 53, 55

[56] References Cited

U.S. PATENT DOCUMENTS

| | | | |
|---|---|---|---|
| 4,328,594 | 5/1982 | Campbell et al. ............................. | 3/7 |
| 4,360,931 | 11/1982 | Hampton ...................................... | 3/32 |
| 4,397,048 | 8/1983 | Brown et al. ................................. | 3/2 |
| 4,547,913 | 10/1985 | Phillips ....................................... | 623/27 |
| 4,822,363 | 4/1989 | Phillips ....................................... | 623/53 |
| 4,959,073 | 9/1990 | Merlette ...................................... | 623/55 |
| 4,994,086 | 2/1991 | Edwards ...................................... | 623/26 |
| 5,116,383 | 5/1992 | Shorter et al. ............................... | 623/53 |
| 5,156,631 | 10/1992 | Merlette ...................................... | 623/52 |
| 5,156,632 | 10/1992 | Wellershaus ................................ | 623/53 |
| 5,181,932 | 1/1993 | Phillips ....................................... | 623/52 |
| 5,181,933 | 1/1993 | Phillips ....................................... | 623/55 |
| 5,217,500 | 6/1993 | Phillips ....................................... | 623/52 |
| 5,290,319 | 3/1994 | Phillips ....................................... | 623/56 |
| 5,486,209 | 1/1996 | Phillips ....................................... | 623/52 |
| 5,509,938 | 4/1996 | Phillips ....................................... | 623/56 |
| 5,514,185 | 5/1996 | Phillips ....................................... | 623/52 |
| 5,514,186 | 5/1996 | Phillips ....................................... | 623/52 |
| 5,529,576 | 6/1996 | Lundt et al. ................................. | 623/27 |
| 5,571,207 | 11/1996 | Houser ........................................ | 623/27 |
| 5,593,445 | 1/1997 | Waits .......................................... | 623/18 |
| 5,593,457 | 1/1997 | Phillips ....................................... | 623/52 |
| 5,653,768 | 8/1997 | Kania .......................................... | 623/27 |
| 5,704,946 | 1/1998 | Greene ........................................ | 623/44 |
| 5,746,773 | 5/1998 | Littig .......................................... | 623/35 |

FOREIGN PATENT DOCUMENTS

| | | |
|---|---|---|
| 1233003 | 2/1988 | Canada . |
| 6225896 | 8/1994 | Japan ..................................... 623/38 |
| 2 202 448 | 9/1988 | United Kingdom . |
| 2 238 247 | 5/1991 | United Kingdom . |
| 2 265 089 | 9/1993 | United Kingdom . |
| WO 94/22398 | 10/1994 | WIPO . |
| WO 95/25488 | 9/1995 | WIPO . |

*Primary Examiner*—Bruce E. Snow
*Attorney, Agent, or Firm*—Fish & Richardson P.C.

[57] ABSTRACT

A single-piece fibre-reinforced plastics shin component for a lower limb prosthesis for a below-knee amputee has an elongate resilient energy-storing blade and, integrally formed at a proximal end of the blade, an alignment plate extending generally anteriorly and perpendicularly with respect to the blade to form at least part of an alignment device for adjusting the position of the blade relative to an upper limb component. The blade is straight and of constant cross-section at least over its distal end portion to allow it to be cut to length to suit the amputee.

24 Claims, 2 Drawing Sheets

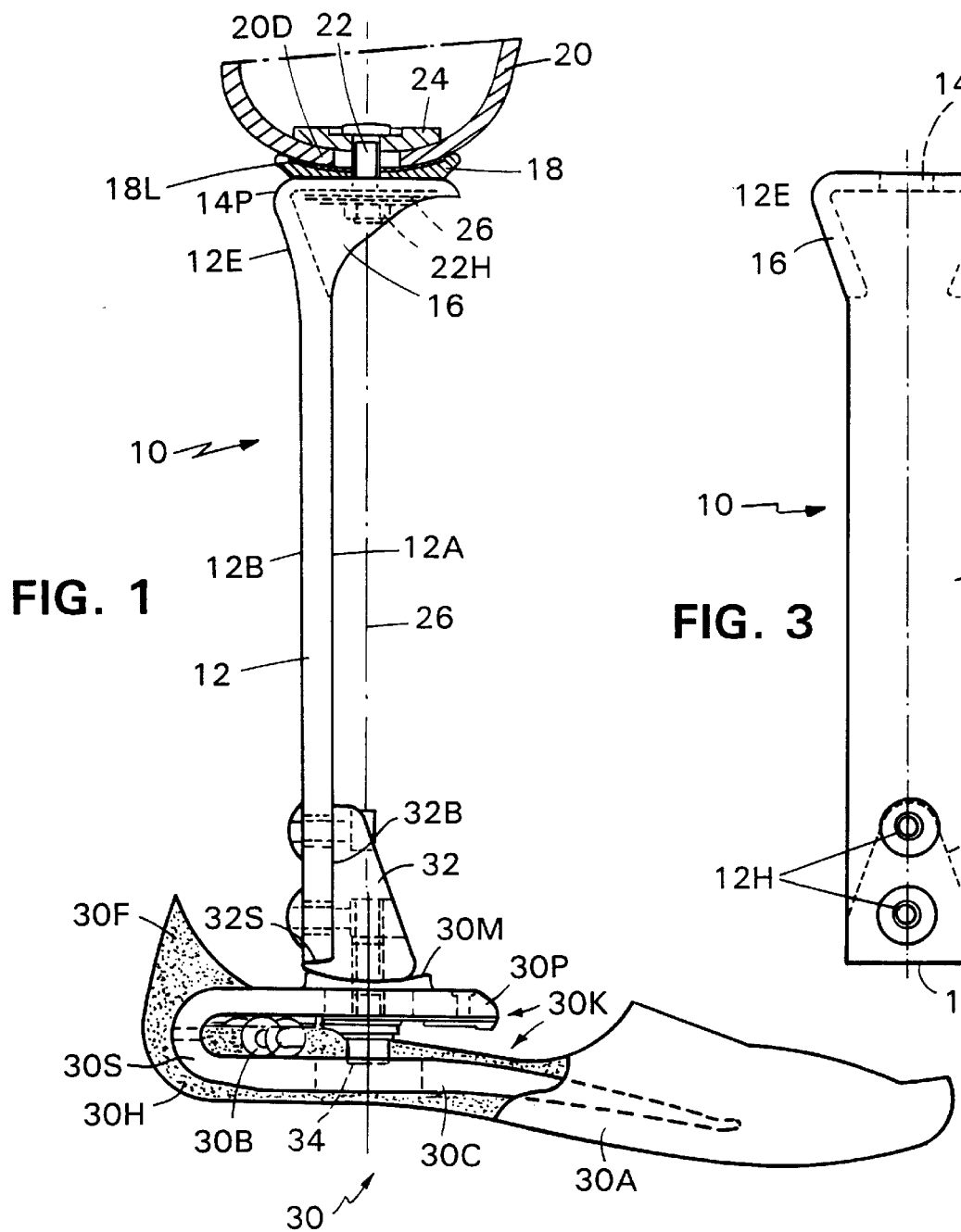

LOWER LIMB PROSTHESIS AND A SHIN COMPONENT FOR THE PROSTHESIS

BACKGROUND OF THE INVENTION

This invention relates to a lower limb prosthesis, and to an energy-storing shin component for the prosthesis.

An energy-storing lower limb prosthesis is known from U.S. Pat. No. 4,547,913 (Phillips). This device provides an integral shin member and forefoot in the form of a single blade of fibre-reinforced material, the shin member extending generally axially of the prosthesis with the forefoot cantilevered in the anterior direction and with a curved connection between shin member and forefoot in an ankle region of the prosthesis. The major surfaces of the blade forming the shin member extend in the medial-lateral direction. A second blade, also with its major surfaces extending in a medial-lateral direction, is rigidly connected to the shin member in the ankle region and extends in the posterior direction to form a resilient heel member. Since the shin member is substantially planar and extends substantially vertically with a cross-section having a high area moment of inertia about an axis generally aligned in the anterior-posterior direction and a relatively low area moment of inertia about a horizontal axis generally aligned in the medial-lateral direction, it acts as a leaf spring storing and releasing energy during the stance phase, by anterior-posterior bending whilst being comparatively rigid with respect to transverse bending moments. This prosthesis is particularly useful for active amputees, including those wishing to take part in sports activities.

A disadvantage of this known device is that the energy-storing capabilities are achieved at the expense of versatility, in the sense that a wide range of sizes and stiffnesses must be produced to suit different amputees, particularly with regard to foot size. Although in the case of below-knee lower limb prostheses, the device may be connected to a stump socket by means of a clamp or flange attached to the proximal end of the shin member, in some situation the length of the shin member becomes comparatively short with consequent loss of energy-storing capacity. This is particularly the case with prostheses for amputees having long below-knee stumps.

It is an object of this invention to provide a versatile shin component for a below-knee prosthesis.

SUMMARY OF THE INVENTION

According to the first aspect of this invention, we provide a single-piece fibre-reinforced shin component for a lower limb prosthesis, comprising an elongate resilient energy-storing blade and, integrally formed at one end of the blade, an alignment element extending generally perpendicularly to the blade to form at least part of an alignment device for adjusting the position of the blade relative to an upper limb component. The alignment element preferably comprises a plate which is generally perpendicular to the longitudinal axis of the blade, the plate being joined to the blade at one edge thereof and extending mainly on one side of the blade. In the preferred embodiment, the plate is joined to the blade at its posterior edge and extends mainly on the anterior side of the blade. At least an end portion of the blade, terminating in an end of the blade opposite to the alignment device, is of constant cross-section with the major faces of the blade being generally planar and parallel to each other at least over the said end portion.

In the case of the alignment element being formed as a plate, the plate may be joined to the blade along a portion of the blade perimeter where the plate forms an angle with the blade and extends generally perpendicularly away from one of the blade major faces. At least one integral reinforcing web may be provided, extending between the blade on one or both sides of the said perimeter portion.

The plate may have a central hole for receiving a bolt for fixing the plate, in the case of a prosthesis for a below-knee amputee, to a stump socket, and the face of the plate directed away from the blade is preferably either planar or part-spherical. With a planar face, the component may be used with a spacer element or washer having one planar face engaging the alignment element of the shin component and a part-spherical face, oppositely directed with respect to the planar face. Whichever configuration is used, a proximally directed part-spherical face is provided as an interface for the stump socket or a component associated with the stump socket Thus, the invention also includes, according to another aspect thereof, a lower limb prosthesis for a below-knee amputee including the combination of a shin component as described above, and a stump socket connected to the alignment element, the connection constituting an alignment interface having interengaging concave and convex surfaces, one of which is associated with the alignment element and other of which is associated with the socket. Generally, when the alignment element is in the form of a plate, the face of the plate directed a way from the blade forms the concave surface. The prosthesis preferably also comprises a bolt which passes through the stump socket and a central hole in the plate, the bolt being releasable so that an aligning adjustment of the relative position of the plate and the socket may be performed. In the preferred embodiment of the invention, the hole in the plate is oversize in the sense that it is larger (in at least one of its transverse dimensions) than the shank of the bolt by a factor of at least two to allow relative translational adjustment of the shin component relative to the socket, as well as rotational adjustment. Where a spacer or washer is provided between the alignment element and the socket, the spacer element also has a hole for the bolt.

According to yet another aspect of the invention, we provide a below-knee lower limb prosthesis including the combination of the above-described shin component and a demountable artificial foot having a foot keel extending in the posterior-anterior direction and an upwardly projecting mounting member for receiving a distal end portion of the shin component blade.

In the preferred embodiment of the invention, this construction allows use of a blade of sufficient length to provide good energy-storing performance for a patient with a relatively long stump, whilst allowing for shin length adjustment by cutting the distal end portion of the shin component to a required length and mounting on the distal end portion an artificial foot of required size and characteristics. Integral construction of the blade and the alignment element yields high strength at the proximal end of the blade whilst providing maximum blade length within the space available.

Assembly of the prosthesis includes the steps of cutting the distal end portion of the blade to a required length, selecting an artificial foot of the required size and configuration, and attaching the foot to the blade end portion by means of a mounting member forming part of the foot, the attachment being formed by, e.g., one or more bolts passing through the mounting member and the blade.

In the case of an above-knee amputee, the shin component may be coupled to a shin cradle which is dimensioned and configured to receive a piston and cylinder assembly for knee joint control, the cylinder being housed between medial and lateral walls of the cradle and pivotally mounted in bosses formed in those walls.

The invention will be described below by way of example with reference to the drawings.

BRIEF DESCRIPTION OF THE DRAWINGS

In the drawings:

FIG. 1 is a diagrammatic side-elevation view, in partial section of a lower limb prosthesis in accordance with the invention;

FIG. 2 is a plan view of the shin component of the prosthesis shown in FIG. 1;

FIG. 3 is a posterior elevation of the shin component of the prosthesis shown in FIG. 1;

DETAILED DESCRIPTION OF THE PREFERRED EMBODIMENTS

Figure 4:
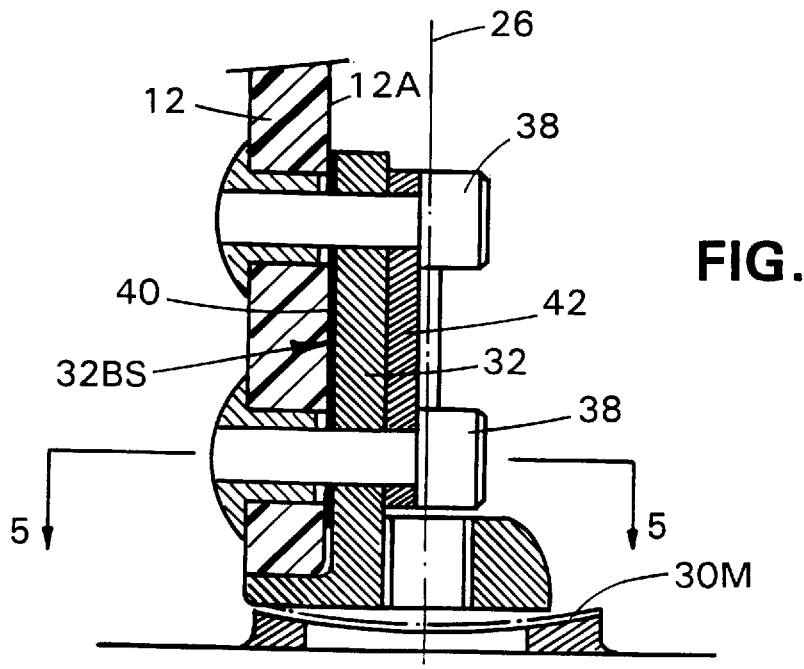
FIG. 4 is a longitudinal cross-section of an alternative shin-foot connection allowing rotational adjustment about both medial-lateral and longitudinal axes.

Referring to FIGS. 1, 2 and 3, a high activity energy-storing lower limb prosthesis for a below-knee amputee has a shin component 10, and a foot component 20 secured to the shin component The shin component 10 is a single-piece moulded carbon-fibre-reinforced plastics component having an energy-storing blade 12 and an integral alignment element in the form of an alignment plate 14 which is substantially perpendicular to the longitudinal axis of the blade 12. Alignment plate 14 is connected as a cantilever to the proximal end of the blade 12 along the posterior edge 14P of the plate.

As will be seen from FIG. 2 the alignment plate 14 has a generally circular perimeter 14C, although the posterior edge 14P is straight where the blade 14 forms a fold line with the blade 12. In a proximal end region 12E the blade 12 is inclined upwardly towards the posterior to meet the posterior edge 14P of the plate 14 at an included angle between 45° and 90°. Being connected to the blade 12 by its posterior edge 14P, the plate 14 extends mainly on the anterior side of the blade 12.

Reinforcing webs 16 extend respectively from the medial and lateral sides of the plate 14 distally to the end region 12E of the blade 12, thereby forming a recess beneath the plate 14. As will be seen from FIG. 3, the webs 16 are flared outwardly and upwardly on account of the width of alignment plate 14 being greater than the width of the blade 12.

In this embodiment, alignment plate 14 has a planar proximal surface which receives a dished spacer element 18 having a corresponding planar lower surface and a concave, preferably part-spherical upper surface for accommodating the convex part-spherical distal surface of a stump socket 20, a frictional layer 18L is secured to the concave surface of spacer 18 to grip the distal socket surface. Connection of the socket 20 to the shin component 10 is performed by means of a bolt 22 which passes through an oversize hole 14H in the alignment plate (see FIG. 2), through the spacer 18, and through an oversize hole in the distal end of the socket 20 inside the socket 20, where the bolt is threaded in a trapping plate 24 which bears against the inside distal wall 20D of the socket. At the distal end of the bolt, the bolt head 22H bears against the distal surface of the alignment plate 14 via a load-spreading washer 26.

Since the holes in the alignment plate 14 and the socket 20 are much larger than required to accommodate the bolt 22, the socket 20 may be adjusted in position relative to the shin blade 12 both translationally, in either medial-lateral or posterior-anterior directions, or angularly by a limited degree of rotation relative to spacer 18. Once a required setting has been achieved, bolt 22 is tightened to clamp the socket 20 to the shin blade 12 between the trapping plate 24 aid the load-spreading washer 26. Access to the head 22H of the bolt 22 is available through the anterior open mouth of the recess between the reinforcing webs 16 of the blade 12. The longitudinal extent of the webs, i.e. their extent parallel to the axis of the blade 12 measured from the distal surface of the alignment plate 14, is no greater than the posterior-anterior extent of the alignment plate 14 and, in this embodiment, no greater than their own posterior-anterior extent adjacent the alignment plate 14.

Figure 6:
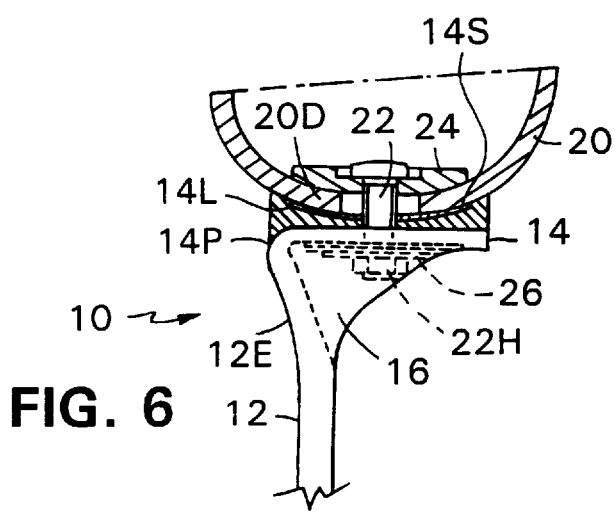
FIG. 6 is a diagrammatic side elevation view, in partial section, of a proximal section of an alternative embodiment of a lower limb prosthesis.

In an alternative embodiment shown in FIG. 6, a proximal surface 14S of the alignment plate 14 is part-spherical like the proximal surface of the spacer 18 in the illustrated embodiment, thereby eliminating the need for a separate spacer. Proximal surface 14S may include a frictional layer 14L similar to frictional layer 18L shown in FIG. 1.

It will be noted that the position of the hole 14H is centered on the longitudinal axis 26 of the prosthesis. Thus, the axis of the hole 14H parallel to the major part of the blade 12 is to the anterior of the blade 12.

In this embodiment, the shin component blade 12 is of rectangular cross-section, having its major surfaces 12A, 12B extending in a medial-lateral direction to allow resilient deformation in response to bending moments acting in the anterior-posterior plane whilst being substantially rigid with respect to bending moments in the medial-lateral plane.

In this preferred embodiment of the invention, the cross-section of the blade is constant over the major part of the blade length, and is, preferably, constant over the whole of its length between the distal end 12D of the blade 12 and the reinforcing webs 16. The width of the blade is between 30 and 50 mm, whilst its thickness is between 7.5 and 15 mm. in this preferred embodiment, the width and thickness are approximately 40 mm and 10 mm respectively.

The blade 12 has a plain distal end portion in the sense that the constant cross-section is maintained to the extreme distal end 12D to allow the blade to be cut to length to suit individual amputees so that the prosthetist is not required to select a shin component from a large range of shin components of different lengths.

The prosthesis includes an energy-storing artificial foot of the configuration disclosed in British Patent Specifications Nos. 2216423 and 2252251, the disclosure of which is incorporated herein by reference.

Foot 30 has a fibre-reinforced plastics keel 30K with an upper mounting plate 20P extending in the anterior-posterior direction, a lower cantilever portion 30C extending from a heel region 30H into an anterior portion 30A of the foot, and a posterior keel portion 30S of C-shaped configuration connecting the upper mounting plate 30P to the cantilever portion 30C in the heel region 30H. Keel 30K acts as an energy-storing spring the stiffness of which can be adjusted, as described in the above-mentioned prior patent specifications, by adjusting the anterior-posterior position of a transverse fulcrum bar 30B located between the distal surface of the upper mounting plate and the proximal surface of the cantilever portion, as shown in FIG. 1.

The mounting plate 30P carries an adjustable shin blade mounting member 32 on a proximally directed concave serrated surface 30M, the mounting member 32 having a convex serrated bearing surface 32B of corresponding radius about a medial-lateral axis. This adjustment interface between the mounting plate 30P of the foot and the mounting member 32 allows adjustment of the angle of the foot about the said axis, providing the possibility of heel height variation. Once a required heel height has been set, the mounting member 22 is rigidly secured to the keel by a bolt 34 centred on the longitudinal axis 26 of the prosthesis.

When the shin component blade 12 has been cut to a required length, fixing holes 12H are drilled so that when the distal end portion of the blade 12 is located in a corresponding recess of the mounting member 32, bolts 38 can be passed through holes in the mounting member, and through tie holes 12H drilled in the blade so as to secure the blade to the mounting member 32. The recess has a distal-proximal planar surface 32B for receiving the anterior surface 12A of the distal end portion of the blade, and is terminated by a locating shoulder 32S which abuts the distal end 12B (sec FIG. 2) of blade 12 when it is located in the recess, thereby defining the overall length of the prosthesis.

The keel 30K of the foot 30 is at least partly surrounded by a moulded foam cosmesis 30F, although alternative ground-contacting members may be provided on the keel, depending on requirements.

Provision of a demountable interface between the blade 12 and foot 30 permits alternative foot configurations to tie combined with the shin component, the integral construction of the blade 12 and alignment plate 14 allowing such foot interchangeability whilst retaining a blade of considerable length and hence superior energy-storing capacity in a prosthesis for a below-knee amputee having a stump of a given length.

The bolt 34 which secures the mounting member 32 to the foot keel 30K, as well as the hole 14H in the alignment plate 14, lie on the longitudinal axis 26. Placement of the shin component blade 12 to the posterior of and parallel to the as 26 has the effect of increasing the strain energy which can be stored in the blade 12 due to the increased moment produced by a ground reaction force in the forefoot (as occurs when the forefoot is loaded during at least the latter part of the stance phase). The strain energy, U, for a beam in pure bending is given by $U=M^2L/2EI$ where E is the flexural modulus of the blade material and I is the second moment of area of the blade section. The moment M is given by FX, where F is the applied load and X is the anterior distance of the point at which load F is applied from the longitudinal axis of the blade. It follows that, for a given load F, the stored strain energy is proportional to $X^2$. This square law illustrates the benefit of locating the blade to the posterior of the limb axis 26.

Figure 5:
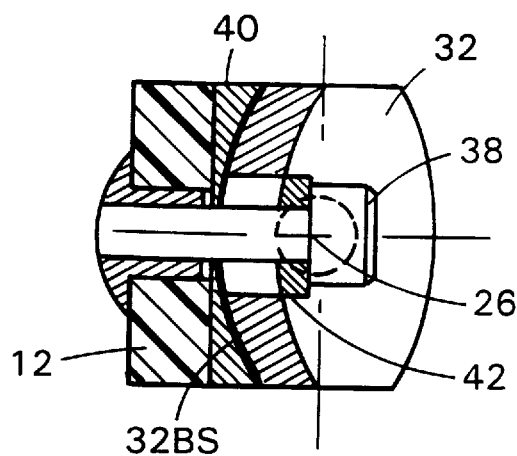
FIG. 5 is a transverse cross-section of the line 4—4 in FIG. 4.

Referring to FIGS. 4 and 5, an alternative structure for connecting the foot 30 to the shin component blade 12 allows adjustment of the angle of the foot not only about a medial-lateral axis, but also about a longitudinal axis coincident with or parallel to the longitudinal axis 26 of the prosthesis, thereby effecting a toe-in/toe-out adjustment. In this case the upper portion of the mounting member 32 has a cylindrical convex posterior bearing surface 32BS centered on an axis parallel and anterior with respect to the prosthesis axis 26. A spacer 40 with a correspondingly cylindrical concave anterior surface and a planar posterior surface is clamped between the mounting member 32 and the anterior surface 12A of the blade 12 when the bolts 38 are tightened. An elongated washer 42 with a convex cylindrical posterior surface transfers the clamping load from the heads of the bolts 38 to a concave cylindrical anterior surface of the upright portion of the mounting member 32. It will be appreciated that by slackening the bolts 38, the upper portion of the mounting member 32, leaving the cylindrical convex and concave surfaces, may be moved from side to side, thereby effecting a rotation of the foot about a vertical axis to the anterior of the limb axis 26. Once a required degree of toe-in or toe-out has been achieved, the bolts 38 are once again tightened.

What is claimed is:

1. A monolithically formed, single-piece fibre-reinforced shin component for a lower limb prosthesis, comprising an elongate resilient energy-storing blade and, integrally formed at a proximal end of the blade, an alignment element extending generally perpendicularly to the blade to form at least part of an alignment device for adjusting the position of the blade relative to an upper limb component, and a reinforcing member extending between the alignment element and the blade for bracing the alignment element with respect to the blade.

2. A shin component according to claim 1, wherein the alignment element comprises a plate which is generally perpendicular to a longitudinal axis of the blade.

3. A shin component according to claim 2, wherein at least a distal end portion of the blade, terminating in a distal end opposite the proximal end is of constant cross-section.

4. A shin component according to claim 2, wherein the blade, at least over the distal end portion, has planar major faces which are parallel to each other.

5. A shin component according to claim 2, wherein the plate is joined to the blade at an edge of the plate, and extends mainly on one side of the blade.

6. A shin component according to claim 2, wherein the plate is joined to the blade at a posterior edge of the plate and wherein the plate extends mainly on an anterior side of the blade.

7. A shin component according to claim 2, wherein the plate is joined to the blade along a portion of a perimeter of the plate where the plate forms an angle with the blade and extends generally perpendicularly away from a major face of the blade, and wherein the reinforcing member includes a web extending between the plate and the blade on one or both sides of the perimeter.

8. A shin component according to claim 2, wherein the plate has a central hole for receiving a bolt for fixing the plate to a stump socket.

9. A shin component according to claim 2, wherein a face of the plate directed away from the blade is planar.

10. A shin component according to claim 2, wherein a face of the plate directed away from the blade is part-spherical.

11. A lower limb prosthesis for a below-knee amputee, comprising:

a monolithically formed, single-piece fibre-reinforced shin component for a lower limb prosthesis, comprising an elongate resilient energy-storing blade and, integrally formed at a proximal end of the blade, an alignment element extending generally perpendicularly to the blade to form at least part of an alignment device for adjusting the position of the blade relative to an upper limb component, and a reinforcing member extending between the alignment element and the blade for bracing the alignment element with respect to the blade; and a stump socket connected to the alignment element, the connection including an alignment interface having interengaging concave and convex surfaces, one of which is associated with the alignment element and the other of which is associated with the socket.

12. A prosthesis according to claim 11, further comprising a spacer element having a first face engaging the alignment element of the shin component, and a second face, oppositely directed with respect to the first face, which has the concave surface.

13. A prosthesis according to claim 11, wherein the alignment element comprises a plate which is generally perpendicular to a longitudinal axis of the blade, and wherein the alignment element has a face directed away from the blade, which face has the concave surface.

14. A prosthesis according to claim 11, wherein the alignment element comprises a plate which is generally perpendicular to a longitudinal axis of the blade, wherein the plate is joined to the blade along a portion of a perimeter of the plate where the plate forms an angle with the blade and extends generally perpendicularly away from a major face of the blade, wherein the reinforcing member includes a web extending between the plate and the blade on one or both sides of the perimeter, and wherein the prosthesis further comprises a bolt which passes through the stump socket and the plate, the bolt being releasable to allow an aligning adjustment of relative positions of the plate and the socket.

15. A prosthesis according to claim 14, wherein a hole in the plate through which the bolt passes is oversize in the sense that it is larger, in at least one of its transverse dimensions, than a shank of the bolt by a factor of at least two to allow relative translational adjustment of the shin component relative to the socket.

16. A prosthesis according to claim 12, wherein the alignment element comprises a plate which is generally perpendicular to a longitudinal axis of the blade, wherein a face of the alignment element plate directed away from the blade is planar, and wherein the spacer element first face is planar and engages the planar face of the alignment element plate, and the spacer element second face is part-spherical and concave and engages a distally directed part-spherical surface on or associated with the stump socket, the bolt passing through a hole in the space element.

17. A lower limb prosthesis, comprising:
a monolithically formed, single-piece fibre-reinforced shin component including an elongate resilient energy-storing blade and, integrally formed at a proximal end of the blade, an alignment element extending generally perpendicularly to the blade to form at least part of an alignment device for adjusting the position of the blade relative to an upper limb component, and a reinforcing member extending between the alignment element and the blade for bracing the alignment element with respect to the blade; and
a demountable artificial foot having a foot keel extending in a posterior-anterior direction and an upwardly projecting mounting member receiving a distal end portion of the shin component blade.

18. A prosthesis according to claim 17, wherein the mounting member is adjustably connected to the keel to allow heel-height adjustment, and is connected to the keel predominantly to the anterior of the blade.

19. A prosthesis according to claim 17, wherein the mounting member is clamped to the blade distal end portion by at least one bolt passing through the mounting member and the blade in an anterior-posterior direction.

20. A prosthesis according to claim 17, wherein the keel comprises a leaf spring.

21. A prosthesis according to claim 20, wherein the keel further comprises an upper mounting portion bearing the mounting member, a lower cantilever portion extending from a heel region of the foot to an anterior portion of the foot, and a posterior portion connecting the upper mounting portion to the cantilever portion in the heel region.

22. A prosthesis according to claim 17, wherein the mounting member has a planar bearing surface for receiving the blade and, adjacent a distal end of the bearing surface, an abutment surface for abutting an end surface of the blade.

23. A method of making a lower limb prosthesis comprising:
providing a monolithically formed, single-piece fibre-reinforced shin component including an elongate resilient energy-storing blade and, integrally formed at a proximal end of the blade, an alignment element extending generally perpendicularly to the blade to form at least part of an alignment device for adjusting the position of the blade relative to an upper limb component, and a reinforcing member extending between the alignment element and the blade for bracing the alignment element with respect to the blade;
selecting a foot prosthesis of a required size and configuration, the foot prosthesis having a foot keel extending in an anterior-posterior direction and an upwardly extending mounting member shaped to receive a distal end portion of the shin component blade;
cutting the distal end portion of the blade to a required length; and
mounting the foot to the shin component by securing the foot mounting member to the blade distal end portion.

24. A lower limb prosthesis comprising:
a monolithically formed shin component in the form of a resilient energy-storing blade having a distal end portion of constant cross-section, and, integrally formed at a proximal end of the blade, an alignment element extending generally perpendicularly to the blade to form at least part of an alignment device for adjusting the position of the blade relative to an upper limb component, and a reinforcing member extending between the alignment element and the blade for bracing the alignment element with respect to the blade; and
a demountable artificial foot having a foot keel extending in a posterior-anterior direction and an upwardly projecting mounting member for receiving the distal end portion of the blade, wherein the mounting member has an alignment interface which is arcuate in a transverse cross-section and engages a corresponding interface of arcuate transverse cross-section associated with the blade, thereby to allow a rotational adjustment of the foot relative to the blade about an axis generally parallel to the lengthwise direction of the blade.

* * * * *